United States Patent
Basin et al.

(10) Patent No.: US 10,005,079 B2
(45) Date of Patent: Jun. 26, 2018

(54) CATALYST HAVING A HELICAL OUTER SHAPE, IMPROVING HYDRODYNAMICS IN REACTORS

(71) Applicants: L'Air Liquide, Société Anonyme pour l'Etude et l'Exploitation des Procédés Georges Claude, Paris (FR); Centre National de la Recherche Scientifique, Paris (FR)

(72) Inventors: Marie Basin, Versailles (FR); Caroline Bertail, Villiers-le-Bâcle (FR); Pascal Del-Gallo, Dourdan (FR); Daniel Gary, Montigny Bretonneux (FR); Amara Fezoua, Lyons (FR); Nik Lygeros, Villeurbanne (FR); Clémence Nikitine, Villeurbanne (FR); Isabelle Pitault, Saint Genis-Laval (FR); Frédéric Bornette, Plan Bourgoin (FR)

(73) Assignees: L'Air Liquide, Société Anonyme pour l'Etude et l'Exploitation des Procédés Georges Claude, Paris (FR); Centre National de la Recherche Scientifique, Paris (FR)

( * ) Notice: Subject to any disclaimer, the term of this patent is extended or adjusted under 35 U.S.C. 154(b) by 0 days. days.

(21) Appl. No.: 15/314,853

(22) PCT Filed: May 27, 2015

(86) PCT No.: PCT/FR2015/051394
§ 371 (c)(1),
(2) Date: Nov. 29, 2016

(87) PCT Pub. No.: WO2015/181494
PCT Pub. Date: Dec. 3, 2015

(65) Prior Publication Data
US 2017/0189896 A1    Jul. 6, 2017

(30) Foreign Application Priority Data

May 30, 2014    (FR) .................................... 14 54934

(51) Int. Cl.
*B01J 21/04*    (2006.01)
*B01J 23/04*    (2006.01)
(Continued)

(52) U.S. Cl.
CPC .......... *B01J 35/026* (2013.01); *B01J 35/023* (2013.01); *B01J 35/1028* (2013.01)

(58) Field of Classification Search
CPC ........ B01J 21/04; B01J 21/063; B01J 21/066; B01J 21/10; B01J 23/04; B01J 23/10;
(Continued)

(56) References Cited

U.S. PATENT DOCUMENTS 2,644,800 A * 7/1953 Mottern ................. B01J 35/026
                                                          422/211
3,673,079 A * 6/1972 Mulaskey .............. B01J 23/755
                                                          208/110
(Continued)

FOREIGN PATENT DOCUMENTS

CN    201 799 279        4/2011
DE        321 078 C1     5/1920
(Continued)

OTHER PUBLICATIONS

International Search Report for corresponding PCT/FR2015/051394, dated Aug. 27, 2015 (with PatentScope translation).
(Continued)

*Primary Examiner* — Patricia L. Hailey
(74) *Attorney, Agent, or Firm* — Elwood L. Haynes

(57) ABSTRACT

A catalyst for catalytic reactors of which the outer shape is a helix with n blades, where n is greater than or equal to 1,
(Continued)

wherein the stack void fraction percentage is between 75% and 85% and the surface area/volume ratio is greater than 1000 square meters/square meters.

8 Claims, 5 Drawing Sheets

(51) Int. Cl.

| | |
|---|---|
| *B01J 23/10* | (2006.01) |
| *B01J 23/28* | (2006.01) |
| *B01J 23/42* | (2006.01) |
| *B01J 23/44* | (2006.01) |
| *B01J 23/72* | (2006.01) |
| *B01J 23/745* | (2006.01) |
| *B01J 23/755* | (2006.01) |
| *B01J 23/881* | (2006.01) |
| *B01J 23/882* | (2006.01) |
| *B01J 23/883* | (2006.01) |
| *B01J 23/885* | (2006.01) |
| *B01J 35/00* | (2006.01) |
| *B01J 35/02* | (2006.01) |
| *B01J 35/10* | (2006.01) |

(58) Field of Classification Search
CPC ... B01J 23/28; B01J 23/42; B01J 23/44; B01J 23/464; B01J 23/6525; B01J 23/72; B01J 23/745; B01J 23/75; B01J 23/755; B01J 23/881; B01J 23/882; B01J 23/883; B01J 23/885; B01J 23/8906; B01J 23/8913; B01J 23/892; B01J 23/8926; B01J 23/8993; B01J 35/00; B01J 2219/302; B01J 2219/304; B01J 2219/31; B01J 2219/30265; B01J 2219/30296
USPC ....... 502/313, 314, 316, 318, 321–323, 326, 502/327, 332–339, 439, 527.24
See application file for complete search history.

(56) References Cited

U.S. PATENT DOCUMENTS

| | | | | |
|---|---|---|---|---|
| 4,289,657 A | * | 9/1981 | Nelson | B01J 35/06 423/212 |
| 4,369,132 A | * | 1/1983 | Kinoshita | B01D 53/945 423/213.5 |
| 4,673,664 A | * | 6/1987 | Bambrick | B01J 35/026 502/439 |
| 4,960,554 A | * | 10/1990 | Bambrick | B01J 35/026 264/219 |
| 2005/0274646 A1 | * | 12/2005 | Lawson | B01J 23/42 208/111.3 |
| 2008/0009408 A1 | * | 1/2008 | Birke | B01J 23/883 502/107 |
| 2011/0053020 A1 | * | 3/2011 | Norton | B01J 21/063 429/425 |
| 2012/0319322 A1 | * | 12/2012 | Barthel | B01J 23/8892 264/177.13 |
| 2012/0322900 A1 | * | 12/2012 | Barthel | C10G 2/33 518/728 |
| 2015/0174571 A1 | * | 6/2015 | Bazer-Bachi | B01J 20/28014 208/253 |

FOREIGN PATENT DOCUMENTS

| | | | |
|---|---|---|---|
| FR | 731 857 | 9/1932 | |
| GB | 26 269 | 11/1913 | |
| NL | 3202 C | 12/1916 | |
| SU | 484 715 | 2/1978 | |
| SU | 797 740 | 1/1981 | |
| SU | 865 361 | 9/1981 | |
| SU | 899 103 | 1/1982 | |
| WO | WO 2005 112552 | 12/2005 | |
| WO | 2015/181494 | * 12/2015 | B01J 19/30 |

OTHER PUBLICATIONS

International Written Opinion for corresponding PCT/FR2015/051394, dated Aug. 27, 2015 (with PatentScope translation).

* cited by examiner

| Shape | Geometry | Number of turns | Length (mm) | Diameter (mm) | S/V ratio of the particle ($m^2/m^3$) |
|---|---|---|---|---|---|
| Helicoid with 1 blade |  | 3 | 10 | 11 | 3144 |
| Helicoid with 1 blade |  | 3 | 30 | 11 | 2620 |
| Helicoid with 1 blade |  | 9 | 30 | 11 | 3108 |
| Helicoid with 2 blades |  | 3 | 15 | 12.5 | 2042 |
| Helicoid with 2 blades |  | 6 | 30 | 12.5 | 1970 |
| Helicoid with 3 blades |  | 5 | 30 | 13 | 2031 |
| Helicoid with 3 blades |  | 9 | 30 | 13 | 3042 |

Radial dispersion – 3 blade / 5 turn helix

Radial dispersion – beads

CATALYST HAVING A HELICAL OUTER SHAPE, IMPROVING HYDRODYNAMICS IN REACTORS

CROSS REFERENCE TO RELATED APPLICATIONS

This application is a 371 of International PCT Application PCT/FR2015/051394, filed May 27, 2015, which claims priority to French Patent Application No. 1454934, filed May 30, 2015, the entire contents of which are incorporated herein by reference.

BACKGROUND

The present invention relates to novel catalyst structures.

A catalyst is a material that converts reactants to product through repeated and uninterrupted cycles of elementary phases. The catalyst participates in the conversion, returning to its original state at the end of each cycle throughout its lifetime.

Currently, commercial catalysts for gas/solid, liquid/solid or gas/liquid/solid processes come in various shapes:
solid shapes (sphere, cylinder, trilobe, quadrilobe, tetrahedron, cube, octahedron, dodecahedron, icosahedron)
hollow shapes (cylinders or multilobes) either pierced by several convex holes of various shapes (circle, angular sector, lobe), or pierced by several non-convex holes such as the internal quadrilobe.

For all these shapes, the hydrodynamics of the reactor is mainly due to the packing of the catalysts and not to their shape, that is to say that the fluid "slides" over the shapes without these shapes generating fluid ejection effects in order to increase the dispersion and the mixing within the bed.

The packing of the catalyst shapes according to the prior art is very porous, has a high void fraction percentage of the packing (PFVE) (>70%) and therefore generates fewer pressure drops. However, the hollow shapes (barrels or miniliths) based on a network of channels having symmetries, result in a packing that, statistically, has numerous preferential pathways. This leads to a low radial dispersion, little turbulence and therefore poor extraparticle material transfers (transfer of reactants) (i.e. transfer of gaseous or liquid phases to the surface of the catalyst), considering gas/solid, liquid/solid or gas/liquid/solid catalytic reactions.

SUMMARY

The present invention proposes to improve the hydrodynamics of fixed-bed reactors for gas/solid, liquid/solid or gas/liquid/solid reactions; on the one hand, by reducing the pressure drops of the fixed beds, on the other hand, by improving the radial dispersion within the reactor.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

One solution of the present invention is a catalyst for catalytic reactors, the shape of which is a helicoid having n blades with n≥1 and is such that the void fraction percentage of the packing (PFVE) is between 75% and 85% and the surface area/volume ratio (S/V) is greater than 1000 m$^2$/m$^3$. The term "blade" will refer to the planar surface attached to the central axis and the term "turn" will refer to the number of rotations of the blades, preferably n=1, 2 or 3.

Note that the helicoid having 1 blade corresponds to the shape that is commonly referred to as an Archimedes screw; the helicoid having 2 blades corresponds to the shape that is commonly referred to as a double helix and the helicoid having 3 blades corresponds to the shape that is commonly referred to as a triple helix, etc.

Each helicoid according to the invention creates turbulences and the use of a packing of helicoids according to the invention leads to phenomena of ejection of gas from one helicoid to another locally improving the mixing within catalytic reactors.

The void fraction percentage of the packing (PFVE) is directly linked to the pressure drop of the catalytic bed. The PFVE is defined as follows:

$$PFVE = 100 - \frac{\text{Volume of the helicoid}}{\text{Total volume of the stack}} \times 100$$

The ratio S/V is defined as follows:

$$S/V = \frac{\text{Surface area of the helicoid}}{\text{Volume of the helicoid}} \times 100$$

Depending on the case, the catalyst according to the invention may have one or more of the following features:
said catalyst has a length between 5 and 40 mm and an equivalent cylinder diameter between 5 and 10 mm;
the surface area/volume ratio (S/V) is greater than 2000 m$^2$/m$^3$;
said catalyst of helicoidal shape comprises between 1.5 and 10 turns;
said catalyst consists of a support of inorganic oxide or mixture of inorganic oxides type;
said catalyst consists of a support and of an active phase deposited on the support;
the support of the catalyst is of inorganic oxide or mixture of inorganic oxides type;
the inorganic oxides are selected from $Al_2O_3$, MgO, CaO, $ZrO_2$, $TiO_2$, $Ce_2O_3$, and $CeO_2$;
the active phase deposited in and/or on the support by all types of techniques (impregnation, co-precipitation, etc.) consists of metal particles selected from Ni, Rh, Pt, Pd, Co, Mo, Cu, Fe and/or a mixture thereof; the active phase may be deposited in and/or on the support by all types of techniques (impregnation, co-precipitation, etc.).

Figure 1:
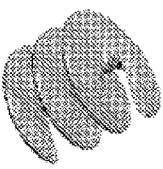
FIG. 1 illustrate examples of catalyst according various embodiments of the present invention.
Figure 1:
Figure 1:
Figure 1:
Figure 1:
Figure 1:
Figure 1:

FIG. 1 gives examples of catalyst according to the invention.

The pressure drops in the catalytic reactors are an essential parameter that influences the performance of certain gas/solid, liquid/solid or gas/liquid/solid processes. The pressure drop in a reactor is linked to the geometry of the catalyst and to the compactness of its packing and/or to the formation of fines during the packing due to its low mechanical strength. Certain gas/solid, liquid/solid or gas/liquid/solid processes involve several catalytic reactors that can have recycles (e.g. the stream leaving a secondary reactor is sent back to the top of a primary reactor). In these cases, compression steps may be necessary and may be detrimental to the overall efficiency of the process if the pressure drops in the reactors are too large. Furthermore, other processes may involve, downstream of the catalytic reactors, units whose performance may be reduced by too low an inlet pressure (e.g. purification units).

The invention proposes novel geometries with high PFVE (greater than 70%) in order to reduce the pressure drops.

Moreover, the gas/solid, liquid/solid or gas/liquid/solid catalytic reactions having rapid intrinsic kinetics are then limited by the transfer of material (transfer of reactants) either from the gaseous or liquid phases to the surface of the catalyst (extraparticle transfer), or from the surface of the catalyst to the active sites within the pores of the catalyst (intraparticle transfer). These material transfers are, in these cases, slower than the reaction and the step limiting the catalytic efficiency is the transport of the reactants to the active site where the reaction takes place.

A key parameter of the catalyst that influences the internal and external transfers is the ratio S/V.

The catalyst according to the invention may be used on any type of reaction (oxidation, hydrogenation, etc.). The main reactions targeted of gas/solid type will be the reactions for reforming a hydrocarbon (natural gas, naphtha, biogas, refinery off-gas, etc.), an alcohol (MeOH, EtOH), or glycerol, via an oxidant such as steam, $CO_2$, oxygen or a mixture thereof, the reactions for converting a synthesis mixture rich in $H_2/CO$ such as the water-gas shift reaction, the reverse water-gas shift reaction, the reaction for synthesizing an alcohol (MeOH, etc.), and the methanation reaction.

The use of the catalyst according to the invention is not limited to gas/solid type reactions but is applicable to liquid/solid and gas/liquid/solid reactions.

The catalyst according to the invention may operate under pressure (1 to 60 at) and at temperature (150-1000° C.).

Finally, another subject of the present invention is a catalytic reactor comprising a packing of catalysts according to the invention.

The advantages of the subject of the invention have been illustrated by the example below.

EXAMPLES

Example 1

Figure 2:
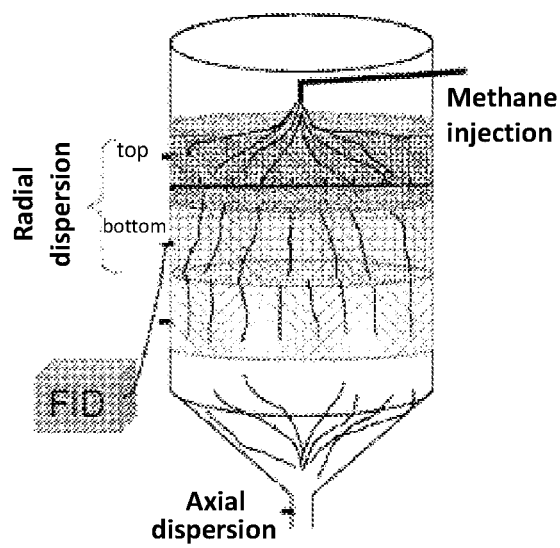
FIG. 2 illustrates a reactor utilizing catalysts, in accordance with one embodiment of the present invention.

Pressure drop and tracing (axial and radial dispersions) experiments were carried out in a reactor with a diameter of 15 cm and a height of 2.5 m (volume of the bed: 46.9 L). This pilot plant has 5 branch connections for the pressure drop measurements and 2 branch connections for the radial dispersion of the gas. The gas phase used is air with a flow rate that may vary from 0 to 185 m³/h (i.e 0 to 2.9 m/s) and the tracer is methane. For the tracing measurements, the methane is injected in a pulsed manner at the top and at the center of the section of the bed (FIG. 2). Regarding the axial dispersions, the concentration of methane is measured by an FID (Flame Ionization Detector) in a cone at the outlet of the reactor with an acquisition frequency of 100 Hz. For the radial dispersions, samplings are taken over the entire diameter of the reactor with the aid of pipes passing through the branch connections of the reactor (FIG. 2). The axial dispersions make it possible to have information on the performance of the reactor (ideal plug flow, dispersed plug flow, etc.) via the measurement of the Péclet number ($Pe=vL/D_{ax}$) with v, the interstitial velocity (m/s), L, the height of the bed (m) and Dax the axial dispersion (m²/s). The higher the Péclet number, the more the reactor tends toward the completely plug-flow reactor. The information on the distribution of the fluid across the bed is obtained by the radial dispersion data.

Subsequently, the following will be denoted:
DP: pressure drops (mbar or Pa)
L: length of the bed (m)
Q: volume flow rate of air (m³/h)
u: superficial (empty tower) velocity (m/s)
v: interstitial velocity (m/s)
ε: porosity of the bed
Dax: axial dispersion (m²/s)
with u=εv The article tested in this example is a helix with 3 blades of 0.4 cm and 5 turns and a length of 3.5 cm. It is compared with commercial articles which are glass beads having a diameter of 5 mm and 10-hole barrels having a diameter of 19 mm and a height of 15 mm with one central 5 mm hole and 9 peripheral 3 mm holes.

Table 1 indicates the pressure drops of the 10-hole barrels as a function of the volume flow rate or the superficial (empty tower) velocity.

Table 2 indicates the pressure drops of the glass beads as a function of the volume flow rate or the superficial (empty tower) velocity.

Table 3 indicates the pressure drops of the helices as a function of the volume flow rate or the superficial (empty tower) velocity.

Figure 3:
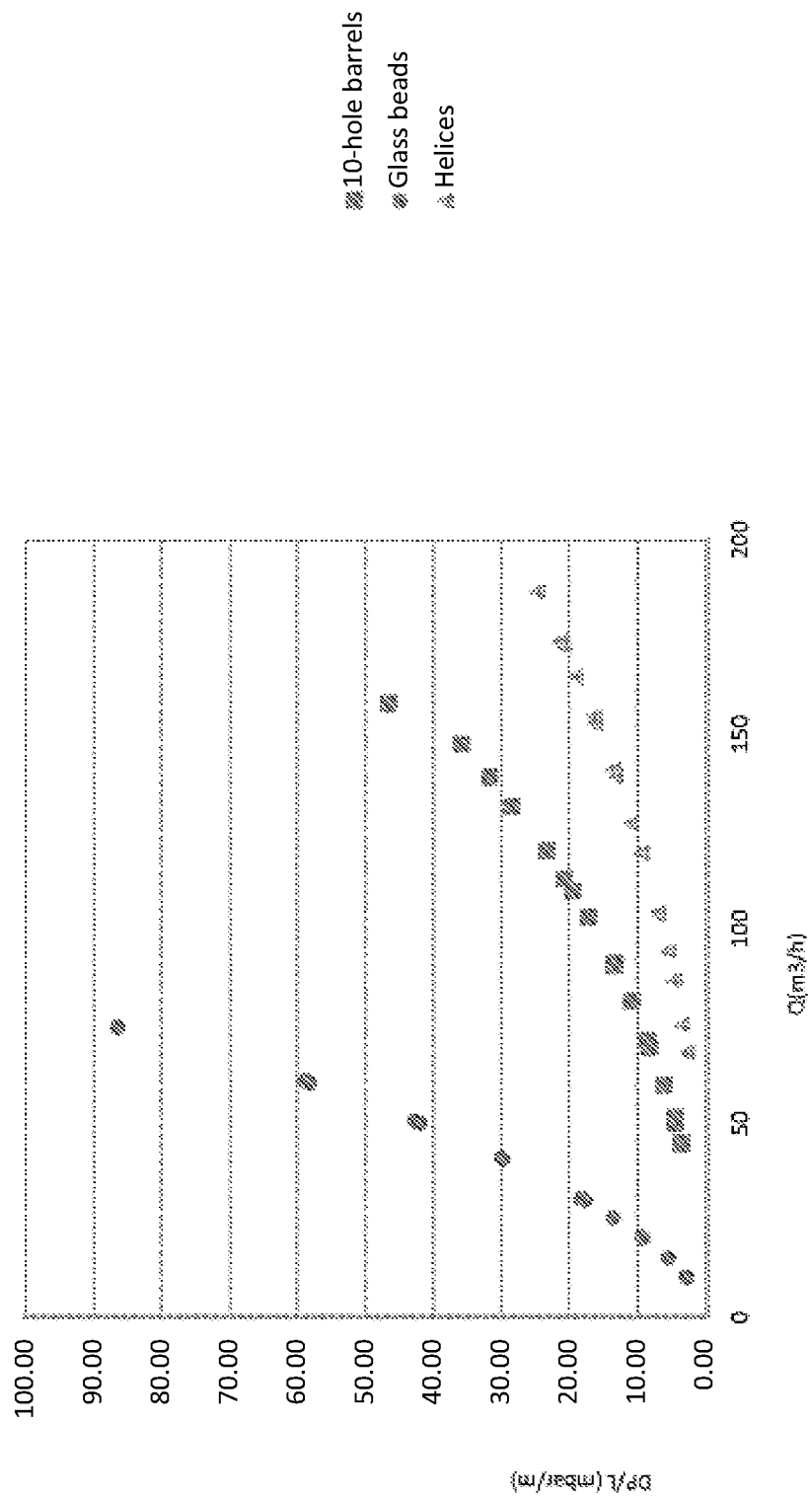
FIG. 3 illustrates the comparative results indicated in tables 1, 2, and 3, in accordance with one embodiment of the present invention.

FIG. 3 enables a comparison of the results given in Tables 1, 2 and 3. The triangles correspond to the pressure drops over the helices, the squares correspond to the pressure drops over the 10-hole barrels and the circles correspond to the pressure drops over the glass beads.

Table 4 indicates the axial dispersion of the 10-hole barrels as a function of the superficial (empty tower) velocity.

Table 5 indicates the axial dispersion of the helices as a function of the superficial (empty tower) velocity.

Figure 4:
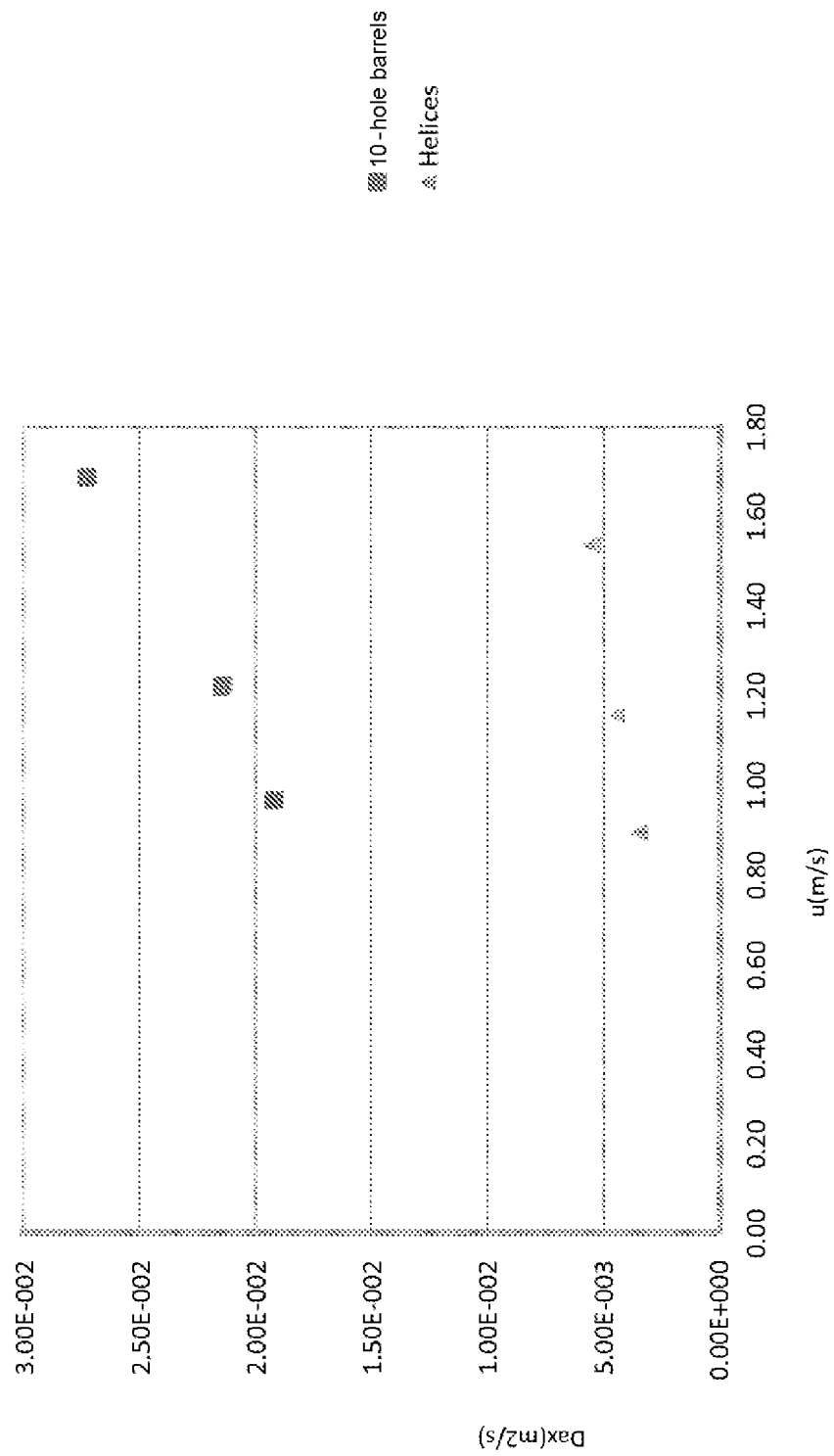
FIG. 4 illustrates the comparative results indicated in tables 4, and 5, in accordance with one embodiment of the present invention.

FIG. 4 enables a comparison of the results given in Tables 4 and 5. The triangles correspond to the axial dispersion for the helices and the squares correspond to the axial dispersion for the 10-hole barrels.

Table 6 indicates the Péclet number determined with a flow rate of 80 m³/h for the 10-hole barrels and the helices.

TABLE 1

| Q<br>m³/h | DP exp<br>mbar/m | DP exp<br>Pa/m | u<br>m/s |
|---|---|---|---|
| 44.95 | 3.80 | 379.64 | 0.71 |
| 49.71 | 4.55 | 455.49 | 0.78 |

TABLE 1-continued

| Q<br>m³/h | DP exp<br>mbar/m | DP exp<br>Pa/m | u<br>m/s |
|---|---|---|---|
| 59.70 | 6.26 | 625.67 | 0.94 |
| 70.99 | 8.71 | 871.23 | 1.12 |
| 81.24 | 11.11 | 1110.68 | 1.28 |
| 90.30 | 13.51 | 1350.56 | 1.42 |
| 102.80 | 17.42 | 1742.35 | 1.62 |
| 109.59 | 19.66 | 1965.68 | 1.72 |
| 119.86 | 23.52 | 2352.19 | 1.88 |
| 131.21 | 28.61 | 2861.28 | 2.06 |
| 147.27 | 36.04 | 3604.31 | 2.31 |
| 157.79 | 46.75 | 4675.35 | 2.48 |
| 138.83 | 31.93 | 3192.52 | 2.18 |
| 112.55 | 20.87 | 2086.86 | 1.77 |
| 90.86 | 13.61 | 1361.49 | 1.43 |
| 69.43 | 8.44 | 844.32 | 1.09 |
| 51.15 | 4.70 | 469.51 | 0.80 |
| 44.48 | 3.67 | 367.00 | 0.70 |

TABLE 2

| Q<br>m³/h | DP exp<br>mbar/m | DP exp<br>Pa/m | u<br>m/s |
|---|---|---|---|
| 10.43 | 2.96 | 296.32 | 0.16 |
| 15.22 | 5.54 | 554.19 | 0.24 |
| 20.42 | 9.11 | 911.37 | 0.32 |
| 25.71 | 13.53 | 1352.53 | 0.40 |
| 30.62 | 18.38 | 1838.29 | 0.48 |
| 41.02 | 29.97 | 2996.83 | 0.64 |
| 50.54 | 42.77 | 4276.65 | 0.79 |
| 60.89 | 58.75 | 5875.13 | 0.96 |
| 74.54 | 86.45 | 8645.15 | 1.17 |
| 60.29 | 58.23 | 5822.83 | 0.95 |
| 50.03 | 41.93 | 4193.42 | 0.79 |
| 40.73 | 29.77 | 2977.50 | 0.64 |
| 30.17 | 17.77 | 1776.67 | 0.47 |
| 20.87 | 9.28 | 928.11 | 0.33 |
| 10.28 | 2.88 | 288.35 | 0.16 |

TABLE 3

| Q<br>m³/h | DP exp<br>mbar/m | DP exp<br>Pa/m | u<br>m/s |
|---|---|---|---|
| 68.06 | 2.69 | 269.01 | 1.07 |
| 75.14 | 3.50 | 350.01 | 1.18 |
| 86.81 | 4.48 | 447.81 | 1.36 |
| 94.18 | 5.55 | 555.16 | 1.48 |
| 103.69 | 7.03 | 703.47 | 1.63 |
| 119.16 | 9.30 | 930.22 | 1.87 |
| 127.04 | 11.00 | 1099.96 | 2.00 |
| 140.86 | 13.59 | 1358.92 | 2.21 |
| 154.61 | 16.43 | 1642.98 | 2.43 |
| 164.74 | 19.17 | 1916.72 | 2.59 |
| 173.90 | 21.42 | 2142.02 | 2.73 |
| 186.51 | 24.81 | 2480.72 | 2.93 |
| 172.42 | 20.80 | 2079.79 | 2.71 |
| 152.62 | 16.27 | 1627.32 | 2.40 |
| 138.98 | 13.15 | 1314.87 | 2.18 |
| 119.37 | 9.64 | 964.11 | 1.88 |
| 104.31 | 6.82 | 682.45 | 1.64 |
| 86.55 | 4.74 | 474.01 | 1.36 |
| 67.97 | 2.68 | 268.30 | 1.07 |

TABLE 4

| v (m/s) | u (m/s) | Dax<br>(m²/s) |
|---|---|---|
| 1.97 | 0.97 | 1.93E−002 |
| 2.49 | 1.22 | 2.15E−002 |
| 3.44 | 1.69 | 2.73E−002 |

TABLE 5

| v (m/s) | u (m/s) | Dax<br>(m²/s) |
|---|---|---|
| 1.13 | 0.89 | 3.39E−003 |
| 1.46 | 1.16 | 4.39E−003 |
| 1.95 | 1.54 | 5.45E−003 |

TABLE 6

| Particle | Axial Péclet number |
|---|---|
| 10-hole barrels (19 × 15 mm) | 280 |
| Helices | 800 |

In summary, the pressure drops are better for the helices than for the 10-hole barrels and the 5 mm beads.

The helices have a higher bed Péclet number than that of the 10-hole barrels (800 and 280 respectively). Consequently, a reactor filled with helices will have an operation closer to that of a completely plug-flow reactor. This result is confirmed by the calculations of the axial dispersions as a function of the superficial (empty tower) velocities. Indeed, as FIG. 4 shows, the axial dispersions (Dax) of the helices are lower than those of the 10-hole barrels, in other words the deviations relative to a completely plug flow are lower with the helices.

Example 2

Radial dispersion measurements were carried out in a tube with a diameter of 15 cm and a height of 80 cm. The tube was filled over 40 cm with the various particles and the measurements were carried out with an air flow rate of 40 m³/h. The experiment consisted in injecting pulses of methane at a height of 28 cm relative to the support grid, the injector being located in the packing. The samplings were carried out using a pipe under the grid for supporting the particles over 9 points per axis (distances with respect to the center: −7.5 cm; −5.5 cm; −3.5 cm; −1.5 cm; 0 cm; 1.5 cm; 3.5 cm; 5.5 cm; 7.5 cm) and over 6 axes spaced apart by 30 degrees (i.e. at 0, 30, 60, 90, 120 and 150 degrees).

The article tested in this example is a helix with 3 blades of 0.4 cm and 5 turns and a length of 3.5 cm. It is compared with commercial articles which are glass beads having a diameter of 5 mm.

Figure 5A:
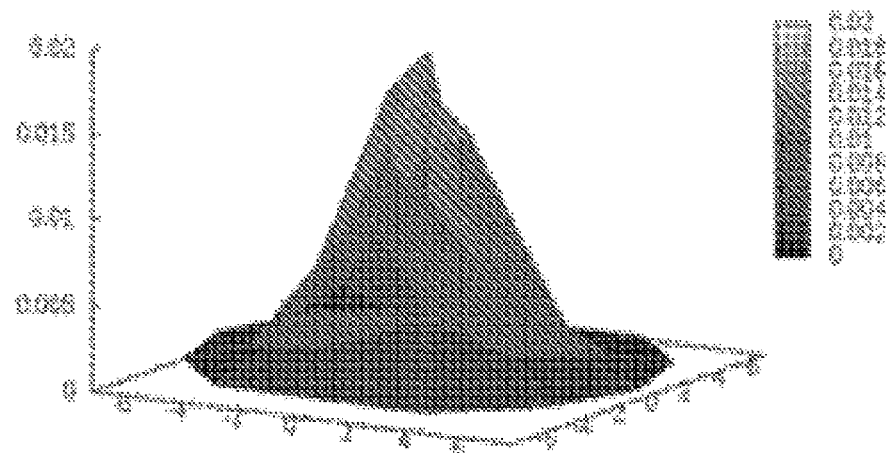
FIG. 5 illustrates that the axial dispersions (Dax) of the helices are lower than those of the 10-hole barrels, in accordance with one embodiment of the present invention.
Figure 5B:
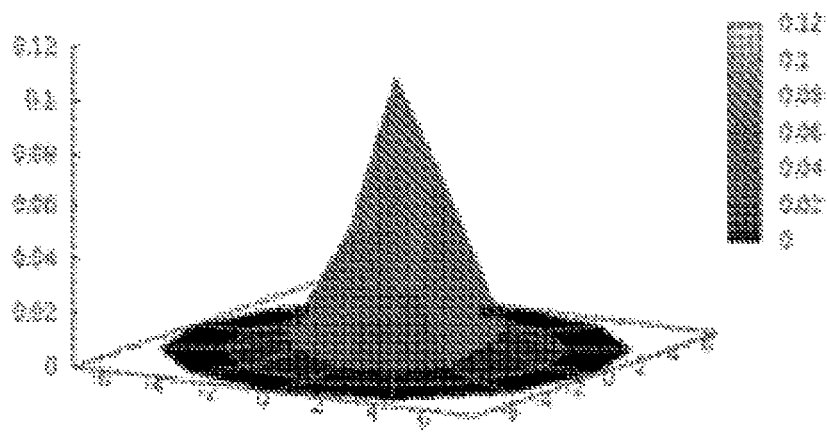

The methane concentration profiles are given in FIGS. 5a) and 5b).

Helix-type shapes greatly improve the radial dispersion of the packings compared to the bead packings. Indeed, the radial dispersion in the helix packing is 50 times greater compared to that of the bead packing.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A catalyst for catalytic reactors, the outer shape of which is a helicoid having n blades with n≥1, wherein the void fraction percentage of the packing is between 75% and 85%, and wherein the surface area/volume ratio is greater than 1000 $m^2/m^3$, with said catalyst comprising a support and of an active phase deposited on the support.

2. The catalyst of claim 1, wherein the catalyst has a length between 5 mm and 40 mm and an equivalent cylinder diameter between 5 mm and 10 mm.

3. The catalyst of claim 1, wherein the surface area/volume ratio is greater than 2000 $m^2/m^3$.

4. The catalyst of claim 1, wherein the catalyst of helicoidal shape comprises between 1.5 and 10 turns.

5. The catalyst of claim 1, wherein the support is of inorganic oxide.

6. The catalyst of claim 1, wherein the inorganic oxides are selected from the group consisting of $Al_2O_3$, MgO, CaO, $ZrO_2$, $TiO_2$, $CeO_2$ and $Ce_2O_3$.

7. The catalyst of claim 1, wherein the active phase consists of metal particles selected from the group consisting of Ni, Rh, Pt, Pd, Co, Mo, Cu, Fe, and a mixture thereof.

8. A catalytic reactor comprising a packing of catalysts as claimed in claim 1.

* * * * *